United States Patent [19]

Borzone

[11] Patent Number: 4,457,306
[45] Date of Patent: Jul. 3, 1984

[54] TOOL AND METHOD FOR ENGAGING TWO MEMBERS OF A JOINT PROSTHESIS

[75] Inventor: Rocco R. Borzone, Emerson, N.J.
[73] Assignee: Howmedica, Inc., New York, N.Y.
[21] Appl. No.: 375,251
[22] Filed: May 5, 1982
[51] Int. Cl.³ .................... A61B 17/00; A61F 5/04
[52] U.S. Cl. ........................ 128/303 R; 128/92 E; 128/321; 128/346; 81/418; 81/421; 81/425 A; 81/426
[58] Field of Search .......... 128/303 R, 321, 346, 128/92 R, 92 E, 92 EA, 92 EC; 81/418, 419, 421, 425 R, 425 A, 426

[56] References Cited

U.S. PATENT DOCUMENTS

| 790,411 | 5/1905 | Watrovs | 81/418 |
|---|---|---|---|
| 1,141,916 | 6/1915 | Aderer | 81/419 |
| 1,536,241 | 5/1925 | Sroka | 81/418 |
| 2,277,081 | 3/1942 | Lillo | 81/419 |
| 2,291,413 | 7/1942 | Siebrandt | 128/321 |
| 2,427,128 | 9/1947 | Ettinger | 128/346 |
| 3,114,367 | 12/1963 | Carpenter et al. | 128/83 |
| 3,801,989 | 4/1974 | McKee | 3/1 |
| 3,818,514 | 6/1974 | Clark | 3/1 |
| 3,840,014 | 10/1974 | Ling et al. | 128/303 R |
| 4,009,712 | 3/1977 | Burstein et al. | 128/92 BA |
| 4,055,172 | 10/1977 | Ender et al. | 128/92 BC |
| 4,075,749 | 2/1978 | Hubeny | 81/426 |
| 4,135,416 | 1/1979 | Roux | 81/421 |
| 4,135,506 | 1/1979 | Ulrich | 128/92 B |
| 4,146,022 | 3/1979 | Johnson et al. | 128/92 B |
| 4,149,439 | 4/1979 | Smith | 81/426 |
| 4,169,470 | 10/1979 | Ender et al. | 128/92 BC |
| 4,197,647 | 4/1980 | Goddenthal | 81/421 |
| 4,240,190 | 12/1980 | Bray | 81/419 |
| 4,263,904 | 4/1981 | Judet | 128/92 B |

OTHER PUBLICATIONS

"Giliberty II Bipolar Endoprosthesis Surgical Technique;" Zimmer, Inc.; pp. 11 and 21 (Jan. 1980).

Primary Examiner—C. Fred Rosenbaum
Assistant Examiner—C. W. Shedd
Attorney, Agent, or Firm—Lawrence C. Akers; Peter C. Richardson; Charles J. Knuth

[57] ABSTRACT

A novel pliers-like tool is disclosed for bringing into engagement the first member, having a head and a neck depending therefrom, and the second member, having a cavity therein receiving said head, of a joint prosthesis. In use, the inner surface of one, preferably bifurcated, jaw of the tool bears against the outer surface of the second member, while the tip of the other jaw bears against the neck of the first member. The two members are readily brought into engagement by closing the handles of the tool.

3 Claims, 10 Drawing Figures

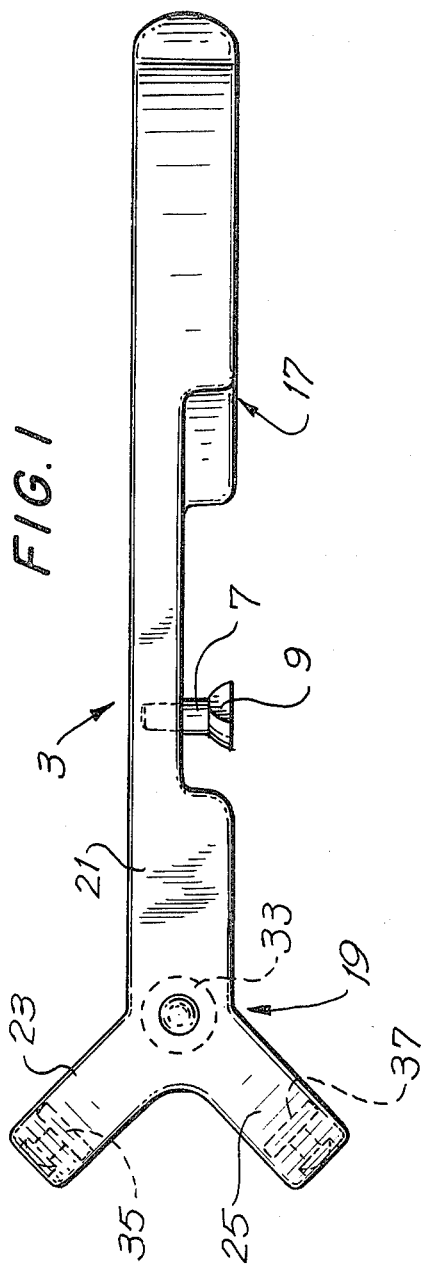
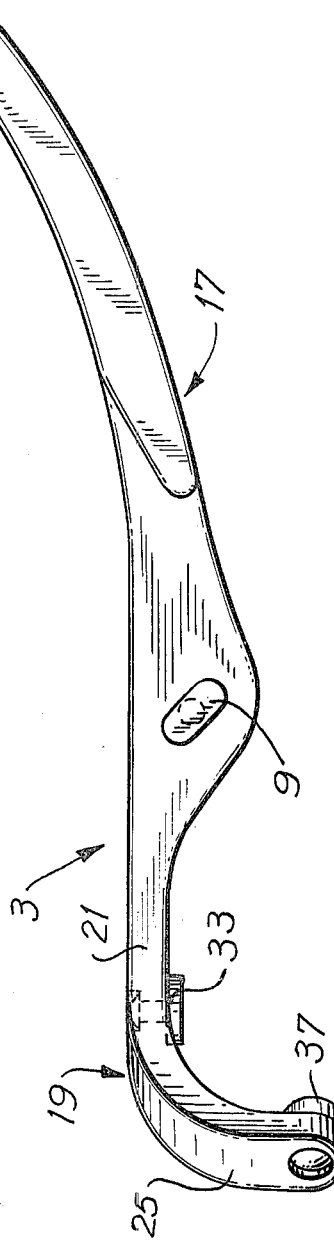
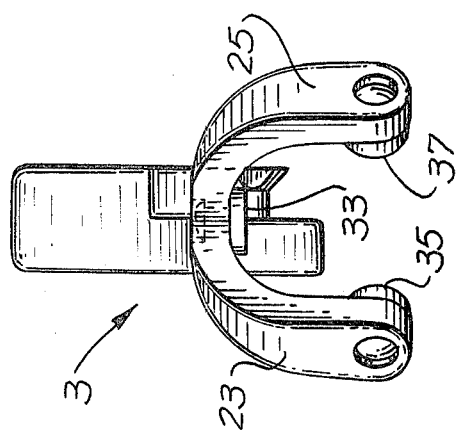

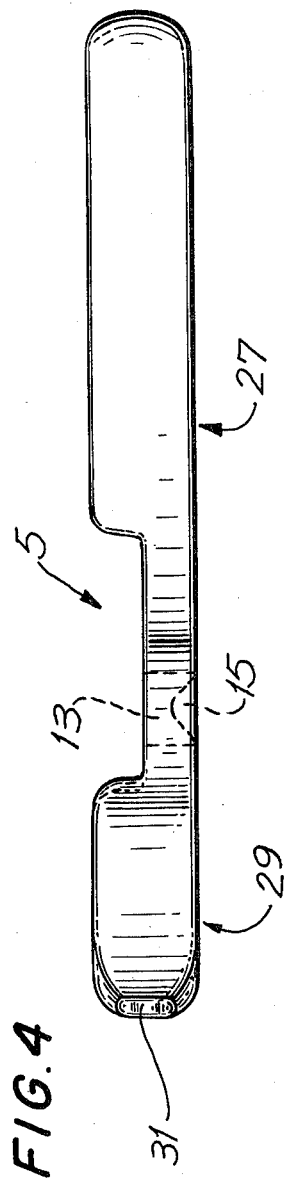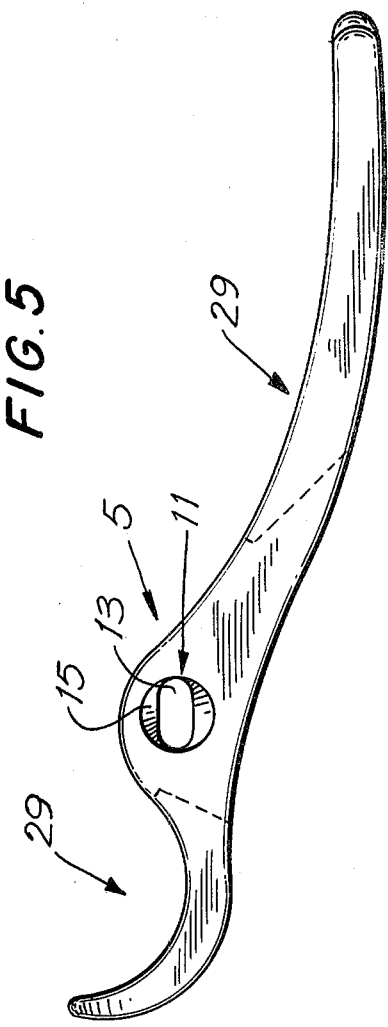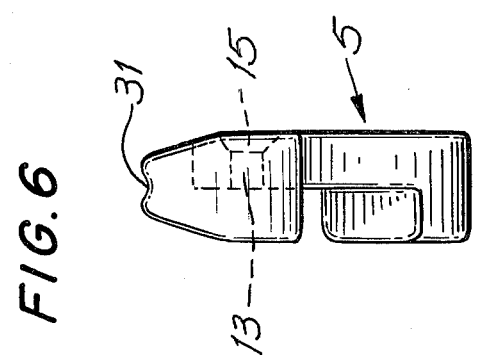

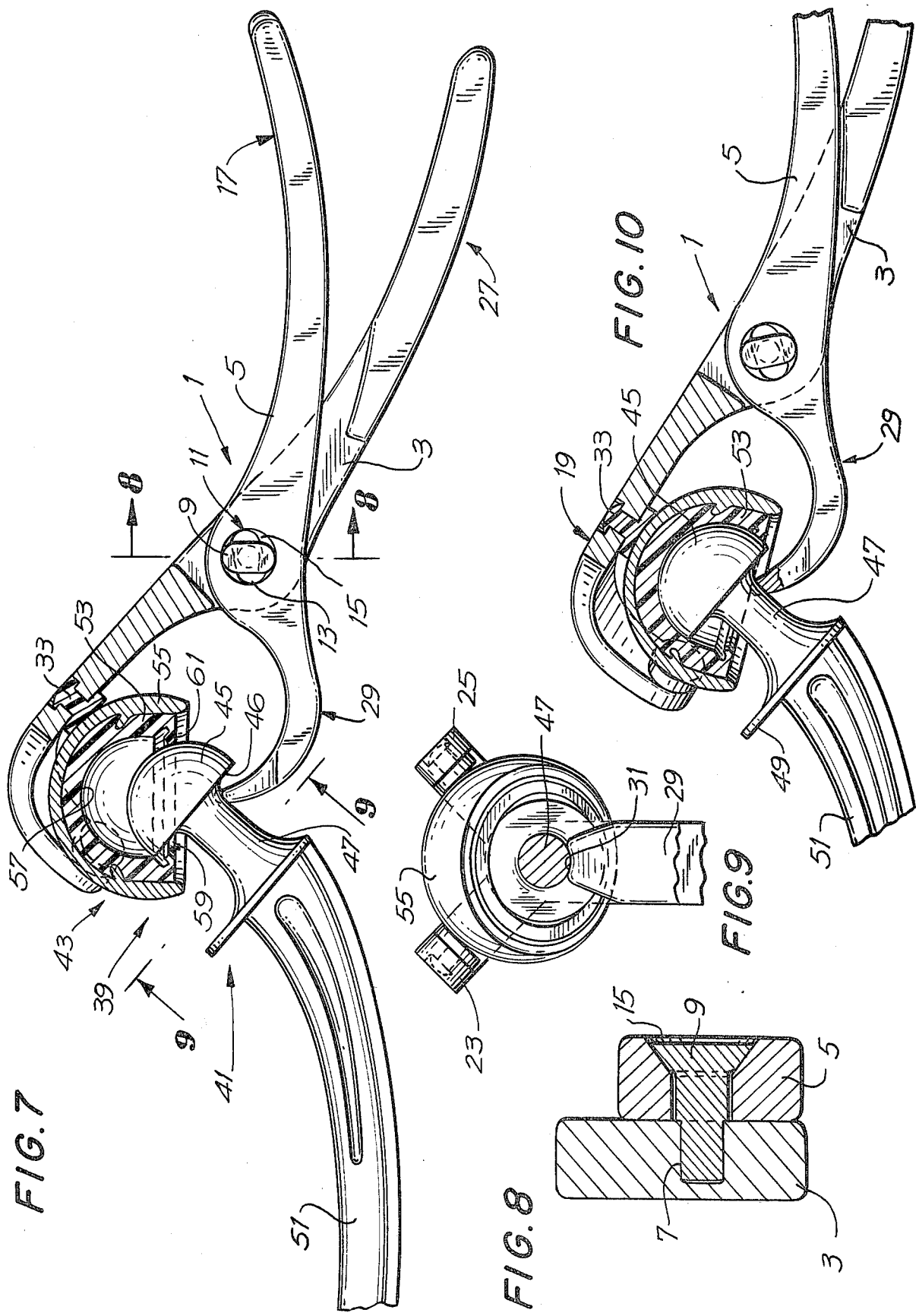

TOOL AND METHOD FOR ENGAGING TWO MEMBERS OF A JOINT PROSTHESIS

BACKGROUND OF THE INVENTION

In the surgical repair of a diseased or damaged hip by implantation of a joint prosthesis, it is often possible to avoid replacement of the natural acetabulum of the patient. In following this conservative approach, it is highly desirable to select a joint prosthesis that will not give rise in use to excessive wear of the acetabular surface. Additionally, it is highly advantageous if the implanted prosthesis is convertible, without damaging its fixation to the patient's femur, for use in articulatory engagement with an artificial acetabular socket, i.e. for use in a conventional total prosthetic hip, should it become necessary at a future time to replace the natural acetabulum with such a socket.

For the above and other reasons, hip joint prostheses comprising a first member adapted to be implanted in the intramedullary canal of the femur and having a metallic spherical head and a second member adapted to receive and hold said head for mutual articulatory engagement therewith have been developed and widely used in recent years with considerable success. The second member typically comprises an outer metallic shell which fits into the natural acetabular socket and an inner plastic cup which is held inside the outer shell and in turn has a cavity formed therein that is substantially congruent with the head of the first member. The inner cup receives the metallic head through a deformable aperture in the cup, which aperture is in communication with said cavity. Since a substantial portion of the motion of the femur is accomodated in use by articulation of the head of the first member within the cavity of the second member, wear of the natural acetabular surface is minimized. The spherical head of the first member is properly sized for mutual articulatory engagement with an artificial acetabular socket and may be exposed for such engagement, if necessary, simply by removing the second member while the first member remains implanted in the femur. An example of such a prosthesis is disclosed in U.S. Pat. No. 4,172,296.

The two members of the type of joint prosthesis described above are engaged by a "snap-fit" as the head passes through a deformable aperture in the plastic cup. Typically, the surgeon may bring the two members into engagement by compressing the members together with his hands. However, this step may sometimes be difficult because the plastic cup, particularly in the region adjacent the deformable aperture, and the metallic head must be precisely dimensioned to permit engagement of the two members but prevent unwanted withdrawal of the head from the cup. Inevitably, a certain amount of dimensional variation is inherent in the commercial scale production of the two members. Furthermore, engagement by hand of the two members with the first member already implanted in the patient's femur, which will be necessary if the surgeon decides to change the size of the second member to obtain a better fit with the natural acetabulum, can prove to be difficult and awkward.

SUMMARY OF THE INVENTION

A novel method for bringing into engagement first and second members of a joint prosthesis, said first member being adapted to be implanted in the body of a patient and having a substantially spherical, non-resilient head and a laterally-curved, non-resilient neck depending therefrom, and said second member having a cavity formed therein substantially congruent with said head, with said second member being adapted to receive said head through a deformable aperture therein for mutual articulatory engagement within said cavity and to hold said head against withdrawal from said cavity, has now been devised. This novel method comprises the steps of providing a tool comprising first and second arms, each having a handle and a jaw, and means for pivotally connecting said arms so that bringing said handles together results in bringing said jaws together, with the jaw of said first arm being curved concavely toward the jaw of said second arm and the jaw of said second arm being substantially shorter than and curved concavely toward the jaw of said first arm, positioning said tool so that the inner surface of the jaw of said first arm bears against said second member and the tip of the jaw of said second arm bears against the neck of said first member, with said head, said aperture and said cavity being generally between said jaws, and bringing said handles together so as to force said head through said deformable aperture. Preferably, in order to improve the tool's grip of the two members of the joint prosthesis, the jaw of the first arm is bifurcated and the tip of the jaw of the second arm is provided with a curved notch which receives the neck of the first member of the prosthesis when said tip bears against said neck.

The present invention includes additionally the novel tool used in the practice of the novel method of the present invention.

The use of the novel method and tool of the present invention provides for a rapid, simple and easy engagement of the two members of the joint prosthesis. This is true even when the first member is already implanted in the patient's body, since in such a case the handles of the tool may be directed to extend out of the body toward the surgeon.

DETAILED DESCRIPTION OF THE INVENTION

The invention will be described in detail with reference to a preferred embodiment of the novel tool and its method of use. Reference to this embodiment and its use does not limit the scope of the invention, which is limited only by the scope of the claims. In the drawings:

FIGS. 1, 2 and 3 are top, side and end elevational views, respectively, of the first arm of a tool of the invention;

FIGS. 4, 5 and 6 are top, side and end elevational views, respectively, of the second arm of said tool;

FIGS. 7 and 8 depict two stages in the method of using said tool, with said first and second arms being pivotally connected;

FIG. 8 is an enlarged sectional view taken along line 8—8 in FIG. 7; and

FIG. 9 is a sectional view taken along line 9—9 in FIG. 7.

A novel pliers-like tool 1 of the invention for bringing first and second members of a joint prosthesis into engagement is shown in FIG. 7. Tool 1 comprises a first arm 3 and a second arm 5 which are pivotally connected so that relative closure of the handles of the two arms results in relative closure of their jaws. Preferably, both handles are slightly curved to conform to the human hand. Tool 1 also comprises the means shown in FIG. 8 for pivotally connecting arms 3 and 5. This means comprises a pin 7 welded into a bore in arm 3 and having an elongated head 9, and an aperture 11 in arm 5 having an inner elongated portion 13 adapted to receive head 9 and an outer circular portion 15 adapted to permit rotation of head 9 therein. Arms 3 and 5 may be readily connected or disconnected by rotating them relative to one another to a fully open position of the tool in which head 9 is aligned with portion 13. During the normal operation of the tool, see for example FIGS. 7 and 10, head 9 rotates within portion 15 of aperture 11 and disconnection of arms 3 and 5 is prevented by the non-alignment of head 9 and portion 13. The particular type of connection means shown in the figures is not critical to the present invention. Any other suitable connection means can be employed, including those that do not permit the ready disconnection of the arms of the tool.

The first arm, arm 3, of tool 1 is shown in detail in FIGS. 1 to 3. Arm 3 includes a handle 17 and a jaw 19 extending in opposite directions from pin 7 to the ends of the arm. Handle 17 and jaw 19 are referred to herein as the first handle and first jaw, respectively, of tool 1. Jaw 19 is curved in a concave-downward manner, i.e. concave toward the jaw 29 of arm 5. Preferably, as shown in the figures, jaw 19 is bifurcated, with trunk 21 branching into prongs 23 and 25 that extend to the free end of jaw 19. When jaw 19 is intended to bear in use against a metallic portion of a member of a joint prosthesis, as will typically be the case, it is preferred to provide a plurality of plastic spacers, e.g. 33, 35 and 37, upon the inner, i.e. lower, surface of jaw 19 so as to reduce the likelihood of scratching or otherwise marring the surface of said metallic portion. These spacers may be "snap-fit" into and held within appropriately configured apertures in the jaw, as best shown in FIGS. 7 and 10, and are preferably made of nylon.

The second arm, arm 5, of tool 1 is shown in detail in FIGS. 4 to 6. Arm 5 includes a handle 27 and a jaw 29 extending in opposite directions from aperture 11 to the ends of the arm. Handle 27 and jaw 29 are referred to herein as the second handle and second jaw, respectively, of tool 1. Jaw 29 is curved in a concave-upward manner, i.e. concave toward the jaw 19 of arm 3, and is substantially shorter than jaw 19. Preferably, as best shown in FIG. 6, a curved notch 31 is provided in the tip of jaw 29.

With the exception of the spacers 33, 35 and 37, arms 3 and 5 are preferably each cast stainless steel pieces. Preferably, pin 7 is separately machined from stainless steel bar stock and, as mentioned above, subsequently welded to arm 3. Additionally, the tip of jaw 29 may comprise a plastic, e.g. nylon, portion (not shown in the figures) which is intended to bear in use against the neck of the first member of the joint prosthesis.

The operation of tool 1 will be described in connection with its use in bringing into engagement the first and second members 41 and 43 of a joint prosthesis 39 (see FIGS. 7, 9 and 10) disclosed in U.S. Pat. No. 4,172,296. Tool 1 may, of course, be used with any other joint prosthesis of the same general type. First member 41 is a unitary, non-resilient metallic article comprising a spherical head 45 having a rearward edge 46, a laterally-curved neck 47 depending from head 45, a shoulder portion 49 and a stem 51 for insertion and fixation within the intramedullary canal of the patient's femur. As used herein, the term "laterally-curved neck" means that the outer surface of the neck is curved convexly in transverse cross-sections. Second member 43 comprises an inner plastic cup 53 which is secured to and surrounded by an outer metallic shell 55 having a substantially spherical outer surface. Cup 53 has a cavity 57 formed therein that is substantially congruent with head 45. Cavity 57 is somewhat greater than a hemisphere and terminates at a deformable circular aperture 59 defined by a resilient annular lip 61 provided in cup 53. In its rest state, aperture 59 has a smaller diameter than cavity 57. As members 41 and 43 are compressed together, lip 61 defining aperture 59 is deformed to allow head 45 to be received within cavity 57 for mutual articulatory engagement with member 43. After head 45 becomes engaged within cavity 57, lip 61 and aperture 59 return substantially to their rest states and hold head 45 against withdrawal from cavity 57.

In use, tool 1, member 41 and member 43 are first positioned with respect to one another substantially as shown in FIG. 7. The arms of tool 1 are adjusted so that spacers 33, 35 and 37 of jaw 19 are in contact with the outer surface of shell 55, the tip of jaw 29 is in contact with neck 47, with said neck being received by notch 31 (see FIG. 9), and head 45, aperture 59 and cavity 57 are generally between jaws 19 and 29. Head 45 is adjacent aperture 59 and tilted so that a segment of rearward edge 46 is beyond lip 61. The surgeon than firmly squeezes handles 17 and 27 together, with his thumb against handle 27 and his fingers against handle 17, to force head 45 into engagement with cup 53 (see FIG. 10). Because of the excellent mechanical advantage provided by tool 1, its simple design and its excellent human engineering, the engagement of the two members of the joint prosthesis is a very easy and reliable procedure for the surgeon to perform.

I claim:

1. A tool for bringing into engagement first and second members of a joint prosthesis, said first member having a substantially spherical head and a laterally-curved neck depending therefrom, and said second member having a cavity formed therein substantially congruent with said head, with said second member being adapted to receive said head through an aperture therein for engagement within said cavity and to hold said head against withdrawal from said cavity, said tool comprising first and second arms, said first arm having a first handle and a first jaw of said tool and said second arm having a second handle and a second jaw of said tool, and means for pivotally connecting said arms so that bringing said handles together results in bringing said jaws together, with said first jaw being bifurcated and curved concavely toward said second jaw and said second jaw being substantially shorter than and curved concavely toward said first jaw, with said second jaw being provided with a curved notch in the tip thereof, said notch being adapted to receive the neck of said first member when said tip bears against said neck, and with a plurality of plastic spacers being provided upon the inner surface of said first jaw for bearing against said second member.

2. A method for bringing into engagement first and second members of a joint prosthesis, said first member having a substantially spherical, non-resilient head and a laterally-curved, non-resilient neck depending therefrom, and said second member having a cavity formed therein substantially congruent with said head, with said second member being adapted to receive said head through a deformable aperture therein for mutual articulatory engagement within said cavity and to hold said head against withdrawal from said cavity, said method comprising the steps of:

(a) providing a tool comprising first and second arms, said first arm having a first handle and a first jaw of said tool and said second arm having a second handle and a second jaw of said tool, and means for pivotally connecting said arms so that bringing said handles together results in bringing said jaws together, with said first jaw being curved concavely toward said second jaw and said second jaw being substantially shorter than and curved concavely toward said first jaw;

(b) positioning said tool so that the inner surface of said first jaw bears against said second member and the tip of said second jaw bears against the neck of said first member, with said head, said aperture and said cavity being generally between said jaws; and (c) bringing said handles together so as to force said head through said deformable aperture.

3. A method for bringing into engagement first and second members of a joint prosthesis, said first member having a substantially spherical, non-resilient head and a laterally-curved, non-resilient neck depending therefrom, and said second member having a cavity formed therein substantially congruent with said head, with said second member being adapted to receive said head through a deformable aperture therein for mutual articulatory engagement within said cavity and to hold said head against withdrawal from said cavity, said method comprising the steps of:

(a) providing a tool comprising first and second arms, said first arm having a first handle and a first jaw of said tool and said second arm having a second handle and a second jaw of said tool, and means for pivotally connecting said arms so that bringing said handles together results in bringing said jaws together, with said first jaw being bifurcated and curved concavely toward said second jaw and said second jaw being substantially shorter than and curved concavely toward said first jaw, with a plurality of plastic spacers being provided upon the inner surface of said first jaw, and with said second jaw being provided with a curved notch in the tip thereof adapted to receive the neck of said first member;

(b) positioning said tool so that said plastic spacers bear against said second member and the tip of said second jaw bears against the neck of said first member, with said head, said aperture and said cavity being generally between said jaws and said neck being received by said notch; and (c) bringing said handles together so as to force said head through said deformable aperture.

* * * * *